US005656170A

United States Patent [19]
Henderson

[11] Patent Number: 5,656,170
[45] Date of Patent: Aug. 12, 1997

[54] OVEN SAFETY FEATURE

[75] Inventor: Robert C. Henderson, Avondale, Pa.

[73] Assignee: Hewlett-Packard Company, Palo Alto, Calif.

[21] Appl. No.: 770,999

[22] Filed: Dec. 23, 1996

Related U.S. Application Data

[63] Continuation of Ser. No. 373,348, Jan. 17, 1995, abandoned.

[51] Int. Cl.⁶ .................................................. B01D 15/08
[52] U.S. Cl. ............................. 210/656; 95/87; 96/102; 210/198.2
[58] Field of Search ........................ 210/656, 175, 210/198.2; 95/87; 96/102

[56] References Cited

U.S. PATENT DOCUMENTS

| | | | |
|---|---|---|---|
| 3,165,147 | 1/1965 | Roof | 96/102 |
| 3,305,000 | 2/1967 | Bullen | 96/102 |
| 3,841,059 | 10/1974 | McCabe | 96/102 |
| 4,038,055 | 7/1977 | Varano | 96/102 |
| 4,181,613 | 1/1980 | Welsh et al. | 210/179 |
| 4,420,679 | 12/1983 | Howe | 219/400 |
| 4,599,169 | 7/1986 | Ray | 210/175 |
| 4,869,876 | 9/1989 | Arfman | 96/102 |
| 4,948,389 | 8/1990 | Klein | 95/87 |
| 5,032,151 | 7/1991 | Klein | 96/102 |
| 5,096,471 | 3/1992 | Sacks | 96/102 |
| 5,108,466 | 4/1992 | Klein | 96/102 |
| 5,141,532 | 8/1992 | Sacks | 96/102 |
| 5,236,593 | 8/1993 | Cortes | 95/87 |
| 5,305,232 | 4/1994 | Chimowitz | 96/102 |
| 5,405,432 | 4/1995 | Snyder | 95/87 |

Primary Examiner—Ernest G. Therkorn
Attorney, Agent, or Firm—Mark Z. Dudley

[57] ABSTRACT

An oven for a chromatograph is shown in which an oven vent is located with respect to an oven fan assembly and an oven vent assembly. In certain operating conditions, the oven fan assembly and the oven vent assembly are controlled by a computer to cause an exchange of cavity air and ambient air to decrease the level of concentration of combustible gases present in the oven.

5 Claims, 2 Drawing Sheets

| FUNCTION | INACTIVE 111 | TRANSITIONAL 112 | ACTIVE 113 |
|---|---|---|---|
| Oven Fan Assembly | Off | On | On or Off |
| Oven Heater | Off | Off for Waiting Period | On |
| Oven Vent Assembly | Open (Air Exchange) | Open (Air Exchange) | Open or Closed |

Fig. 2

OVEN SAFETY FEATURE

CROSS REFERENCE TO RELATED APPLICATIONS

This is a continuation of application Ser. No. 08/1373,348 filed on Jan. 17, 1995, now abandoned.

FIELD OF THE INVENTION

The present invention relates to methods and apparatus for safe operation of a heated zone in an analytical apparatus, and more particularly with a gas chromatograph having an oven that is subject to containment of a combustible gas.

BACKGROUND OF THE INVENTION

The basic components of a gas chromatograph include an injection port for introducing a sample of matter to be examined into a stream of carrier medium, a column attached to the injection port and constructed in the form of a helix of tubing containing chemicals that cause some of the constituents of the sample to elute at different times, a temperature-controlled zone in which the column is mounted, and a detector for producing a signal indicative of the concentration of the constituents being eluted. An integrator may be employed for integrating the signal so as to provide information as to the quantity of each constituent.

In the typical gas chromatograph, the temperature-controlled zone is constructed as an oven. The injection port and detector are attached to respective pneumatic fittings on the oven, and the separation column is attached between the pneumatic fittings and located within the oven. The oven typically comprises a thermally insulated oven housing having a door to permit access to the oven interior, a controlled heating element, and a motor-driven stirring fan. The stirring fan continuously mixes the air contained within the oven housing so as to minimize temperature gradients therein that could adversely affect the performance of the chemical process occurring within the column. In analyzing most samples, the heating element is controlled so as to increase the temperature of the oven from a minimum initial value to a maximum final value. Before introduction of the next sample into the column, the temperature of the oven is returned to its initial value. Whereas rapid cooling can be effected by simply opening the door, this heats up the front surfaces of the oven to an objectionable degree. Accordingly, it is known to operate the stirring fan to draw cool ambient air into the oven through an intake port and to expel hot air from the oven through an exhaust port in such manner as to avoid heating the outer surfaces with which the operator is likely to come in contact.

Some gas chromatographs employ combustible gasses such as hydrogen as the carrier gas or detector gas. Even though the injection port, detector, separation column, and pneumatic fittings in the typical chromatograph are designed to minimize leakage of such a combustible gas into the oven interior, one may nonetheless consider a pneumatic fault mode wherein a gas leak could occur and sufficient gas could accumulate in the oven so as to pose an unsafe condition.

SUMMARY OF THE INVENTION

I have determined that an unsafe condition can occur in some conventional gas chromatographs, one that typically occurs with the presence of a combustible gas in an oven when the oven door is closed, the stirring fan is off, and the oven is hot. In accordance with this invention, the oven air is exchanged with ambient air during certain operating conditions that may otherwise pose a combustion hazard. The concentration of any combustible gasses, if present, are thereby reduced below a hazardous level, thus providing for safe operation of the chromatograph.

The advantages of the invention are achieved in a first preferred embodiment of the chromatograph that includes an oven including a oven housing having walls defining a cavity and a volume of cavity air within the oven housing; an oven heater, selectably operable in response to the computer for heating the cavity air; an oven vent located in the oven housing so as to communicate between the cavity and ambient air; and an oven vent assembly selectably operable in response to the computer for allowing an exchange of cavity air and ambient air through the oven vent, and a computer for determining one of a plurality of oven operating conditions, and, in response to a determination of the operating condition, controlling the operation of said oven heater and said oven vent assembly. The plurality of operating conditions includes an inactive oven condition, wherein the computer operates the oven vent assembly to effect an exchange of cavity air with ambient air during the inactive oven condition.

In another preferred embodiment of the chromatograph, the plurality of operating conditions also includes a transitional oven condition, wherein the computer withholds the operation of the oven heater for the duration of a waiting period, and operates the oven vent assembly to effect an exchange of cavity air with ambient air during the waiting period.

In another preferred embodiment of the chromatograph, there is provided an oven fan that is operable under control of the computer for facilitating the exchange of cavity air with ambient air during the inactive oven condition or the transitional oven condition.

BRIEF DESCRIPTION OF THE DRAWINGS

The present invention will be better understood, and its numerous objects and advantages will become apparent by reference to the following detailed description of the invention when taken in conjunction with the following drawings, in which:

FIG. 2 is a state diagram representing the control of a plurality of functions associated with the operation of the gas chromatograph of FIG. 1 during each of several operating conditions.

DETAILED DESCRIPTION OF THE PREFERRED EMBODIMENT

Figure 1:
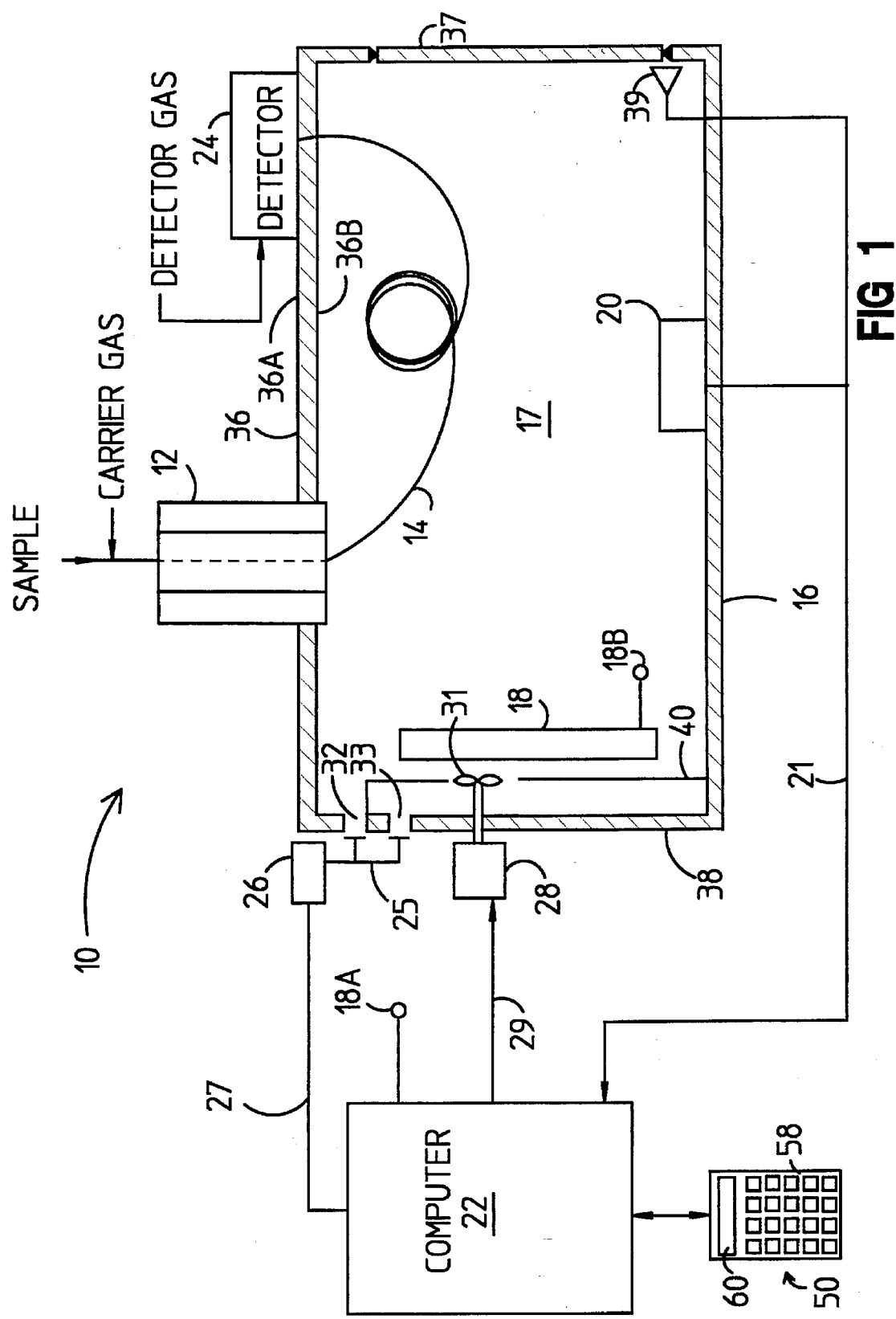
FIG. 1 is a simplified block diagram of a gas chromatograph constructed in accordance with the present invention.

A new and novel gas chromatograph is shown in FIG. 1 and is generally designated 10. In the preferred embodiment, the gas chromatograph 10 is a Hewlett-Packard 6890 gas chromatograph. The chromatograph 10 is arranged to perform a chromatographic separation of a given sample compound in a sequence of events that may be termed an analytical "run".

The illustrated embodiment utilizes a sample injection technique with a pressurized carrier gas by means of an injection port 12. The carrier gas supplied to injection port 12 is provided from a source through an appropriate valve (not shown), which serves to control the pressure of the carrier gas in the gas chromatograph 10. However, for the purposes of this description, the sample may be considered as being injected using any conventional technique.

A separation column 14 is positioned within an oven 16 having an oven cavity 17, a heating unit 18, and a temperature sensor 20. Heating unit 18 provides heat to oven 16 in response to a control signal generated on control line 18A, 18B by computer 22, as will be described in greater detail herein. In order to ensure that the temperature within the oven 16 is at a desired level, sensor 20 generates a feedback signal representative of the temperature in oven cavity 17, which signal is provided on a signal bus line 21 to computer 22. The carrier gas/sample combination passing through column 14 is exposed to a temperature profile resulting in part from the operation of oven heater 18 within the oven 16. During this profile of changing temperatures, i.e., rising or falling, the sample will separate into its components primarily due to differences in the volatility characteristics of each component at a given temperature. As the components exit column 14 they are detected by detector 24. Detector 24 can be any of the known detectors, such as a flame ionization detector or a mass spectrometer.

The particular embodiment of the oven 16 is illustrated in the form of an oven housing that preferably includes an oven wall 36. Thermal insulation fills the oven wall 36 between an outer metal shell 36A and an inner metal shell 36B. The oven heater 18, an oven vent assembly 26, and an oven fan assembly 28 can be located at any side of the oven 16, but as shown they are located opposite an oven door 37 at a rear wall 38. The oven vent assembly 26 includes flaps 25 and control line 27 and the oven fan assembly 28 includes fan assembly control line 29 and an oven fan 31. An oven vent, preferably in the form of an exhaust port 32 and an intake port 33, is provided in the rear wall 38. The intake and exhaust ports 33, 32 are preferably provided as cylindrical airways that extend through the rear wall 38. The intake and exhaust ports 33, 32 may be selectably opened or closed by selected positioning of the flaps 25 by known driving means in the oven vent assembly 26.

It is contemplated that the oven door 37 is located to allow access to the oven cavity 17. The position (open or closed) of the oven door 37 is sensed by a door sensor 39 and an appropriate signal is provided on the signal bus 21. When the flaps 25 are positioned to cover the intake and exhaust ports 33, 32, and when the door 37 is closed, the oven 16 defines a substantially closed, thermally-insulated volume of air which, for convenience, will be termed the cavity air.

The oven fan 31 is mounted on a shaft extending through the rear wall 38 and is rotatable by known means in a selected direction. A rear wall 40 of the oven defines a circular opening about the oven fan 31. In the preferred embodiment of the oven vent, the oven fan 31 is rotated in a direction so as to move cavity air through the exhaust port 32 and the intake port 33 is used to allow ambient air to enter the cavity 17. If the oven fan 118 were rotated in an opposite direction, the reverse would be true. Although not shown, a duct may be provided to the exhaust port 32 so as to prevent hot exhaust air from being immediately drawn into the intake port 33. The oven heater 18 is mounted by tabs (not shown) in a plane parallel to the rear wall 40 and the door 37 at a point just forward of the fan 31. The oven heater 18 has one or more central openings through which cavity airflow may occur in a stirring fashion. The oven fan assembly 28, oven heater 18, and oven vent assembly 26 are operable to provide such a cavity air stirring function, e.g. for temperature control of the oven cavity, as described in commonly-assigned U.S. Pat. No. 4,181,613, VENTING METHOD FOR A CHROMATOGRAPH OVEN, the disclosure of which is incorporated herein by reference. However, and in a departure from the prior art as will now be described in detail, the oven vent assembly 26 is selectively employed by the computer 22 in conjunction with the operation of the oven fan assembly 28 to cause an exchange of air through the oven cavity 17 during certain operating conditions not contemplated by the prior art. The contemplated exchange of cavity air with ambient air serves to dilute any combustible gases present in the oven cavity. We may now consider that portion of the operation of computer 22 which especially relates to and is in accordance with the present invention, that is, a description of procedures that are invoked so that analytical runs can be reliably conducted without the hazard of an aggregation of combustible gasses in the oven cavity 17.

Computer 22 maintains overall control of a plurality of functions associated with the operation of the gas chromatograph 10. Although computer 22 is shown as a single block, such computer is preferably a printed circuit board assembly and includes a central processing unit and all associated peripheral devices, such as random access memories, read-only memories, input/output isolation devices, clocks, drivers, interface circuits, and other related electronic components. In the preferred embodiment, the central processor used in computer 22 is a programmable microprocessor. As such, computer 22 includes a memory in which information and programming, directed to a plurality of control functions can be stored and retrieved by known methods. Such control functions include control of the oven vent assembly 26, the oven fan assembly 28, and the oven heater 18. In particular, such information, programming, and control functions are contemplated as being directed to operation of the chromatograph 10 during certain operating conditions that are subject to hazardous accumulation of combustible gasses.

Accordingly, the chromatograph 10 includes a control panel 50 connected to computer 22. The control panel 50 includes data entry devices such as a keypad 58. Various pieces of information may entered into computer 22 by the user through way of keypad 58, and computer 22 operates to act upon the entered information or to store the entered information into memory for later access. Operating commands, which allow selection of operating modes that cause the operating conditions of the chromatograph to change, and other information may thus be entered into computer 22. For example, a request to initiate an analytical run, and the entry of operating parameters relating to the analytical run (such as the temperature profile to be provided by oven 16 during the analytical run) may be entered using keyboard 58. In the preferred embodiment, the control panel 50 is provided with a display screen 60. Consequently, indicating or prompt messages can be generated by computer 22 and displayed on the display screen 60.

The computer 22 provides coordinated control of oven heater 18, the oven vent assembly 26, and the oven fan assembly 28. The computer 22 in the preferred embodiment monitors the operating condition of the chromatograph 10 and generates control signals in a digital form which are buffered and directed to one or more devices under control, such as the oven vent assembly 26. A plurality of operating conditions and control signals are contemplated. The computer 22 controls operation of the oven vent assembly 26 by transmitting a drive signal on control line 27 which causes the oven vent assembly 54 to move flaps 25 to selectively position the flaps 25 relative to the intake and exhaust ports 32, 33 thus controlling the exchange of cavity air with air from the ambient environment. The computer 22 controls the oven heater 18 by transmitting a drive signal on control lines 18A, 18B to oven heater 18. Sensor 20 senses the temperature in oven 16 and transmits a feedback signal representative of such temperature to computer 22. The computer 22 controls operation of the oven fan assembly 28 by transmitting a drive signal on control line 29 which activates or deactivates the fan assembly 54, thus changing the cavity airflow through oven heater 18 and causing heat to be transferred to the cavity air in the oven cavity 17.

The computer 22 also maintains information relevant to the potential concentration of combustible gasses in the oven cavity. Such information, for example, may include the current oven operating condition, the operation and direction of rotation of the oven fan 31, the state (open or closed) of the oven door 37, or the degree of closure of the intake or exhaust ports by the flaps 25 in the oven vent assembly 26. As will be described below, by monitoring the operating conditions in the gas chromatograph 10, and assembly 26 and the oven fan asset assembly 26 and the oven fan assembly 28, the computer 22 can dilute the concentration of any combustible gasses that may be present in the oven cavity 17 below some desired level.

In the preferred embodiment, the current and desired operating conditions for any given moment in time during the operation of the chromatograph 10 are calculated by computer 22 in relation to inputted and stored information, such as the oven temperature profile parameters. Having calculated such operating conditions, the computer 22 then generates a variety of the desired control signals in real time. For example, the actual temperature of oven 16 is known from sensor 20, and the actual states of the flaps 25, oven door 37, oven fan 31, and oven heater 18 are known. Computer 22 may thereby regulate the flow of ambient air into the oven cavity 17, and the flow of cavity air about the oven heater 18 to establish the desired temperature in the oven cavity 17.

In performing an analytical run, samples of the matter to be analyzed are supplied to the injector port 12 wherein they are mixed with a carrier gas before being applied to one end of the column 14. In accordance with conventional practice, when the sample is injected into the column 14, the oven door 37 is in a closed state, the flaps 25 are typically positioned so as to cover the intake and exhaust ports 32, 33 (i.e., in a closed position), and the signal to the oven heater 18 is programmed by the computer 22 so as to increase the temperature of the oven from low initial value to a high final value. The fan 31 is then operated as a stirring fan, that is, it draws hot air to it from within a first zone in the oven cavity including the central portion of the oven cavity 17, and directs it along intermediate paths that extend along the blades of the fan 31 in a generally outward direction and pass through the oven heater 18. After passing through the oven heater 18, the air reenters the first zone. Thus the stirring flow of air in the oven cavity is in the form of a vortex. During an operating condition when the oven temperature is to be maintained at a near-ambient temperature, the position of the flaps 25 may be varied to a partially open position such that portion of the hot air flowing in some of the intermediate paths is directed out the exhaust port 32. This creates a partial vacuum in the space defined by the intake port 33 so as to draw in cool ambient air. The cool ambient air merges with the portion of the hot air flowing in the intermediate paths that was not intercepted, thus effectively setting the ratio between hot exhaust air and entering cool ambient air as is required, so as to alter the temperature of air in the oven cavity 17. The power supplied to the oven heater 18 may be controlled by the computer 22 so as to warm the mixture of cold and hot air as needed. The flaps 25 can also be rotated to any desired position by the oven vent assembly 26 in response to control by the computer 22. The analytical run continues such that activity within the column 14 causes various constituents in the sample gas to elute from the column 14 to the detector 24 at different times. The elutants are discerned by the detector 24, and a signal related to their concentration is produced. The signal from the detector is usually applied to an integrator, not shown, for determining the quantity of the matter eluted. The analytical run in thereby considered as having been completed.

Before the next sample is introduced into the column 36, the oven is typically cooled and stabilized at an initial temperature that is usually above ambient air temperature. To do this as rapidly as possible, the flaps 25 are fully opened. A portion of the hot air flowing in some of the intermediate paths is directed out the exhaust port 32; cool ambient air merges with the portion of the hot air flowing in the intermediate paths that was not intercepted, thus effectively cooling the oven cavity 17. Upon attaining the desired initial temperature, the computer 22 may be programmed to close the flaps 25, thus preventing the ambient conditions to alter the initial temperature.

At such time, the operator of the unit is typically engaged in other work, such as the preparations required for performing another analysis, and may decide to set the oven 16 to an inactive condition. Inactivation of the oven is contemplated as being initiated by the operator upon entry of the appropriate command on the keypad 58 to inactivate the oven heater 18, although other events may trigger such a condition. For example, the computer 22 may determine that a particular operating condition necessitates that the oven 16 be inactivated, such as the opening of the oven door 37 while the oven heater 18 or the oven fan 31 is active, or as may be required during a failure or fault mode, and the computer 22 is programmed to act accordingly.

However, a considerable amount of time may pass before the oven 16, which is an enclosed volume, is again opened to the ambient air. As described in the Background of the Invention, one of the preferred gases used with most chromatographs, including the illustrated gas chromatograph 10, is pressurized hydrogen. Heretofore, in the event of a failure in a pneumatic component, such as the injector port 12 or the detector 24, or upon the fracture of the column 14, hydrogen gas would tend to accumulate in the enclosed volume defined by the oven cavity 17 and reach a level sufficient for an explosion to occur in the event of a spark, or upon contact with a heated surface (such as the oven heater 18) when the oven heater 18 is again activated. It is contemplated that the concentration of hydrogen would be highest during what may be considered as a worst-case condition, wherein the door 37 and the flaps 25 are closed and the oven fan 31 is inactive.

As denoted by the state diagram 100 shown in FIG. 2, and in a departure from the conventional practice, the computer 22 is programmed to control certain functions 110 according to at least one of three oven operating conditions (inactive 111, transitional 112, active 113). In particular, the computer 22 operates the oven vent assembly 26 to allow an exchange of cavity air with ambient air when the oven 16 is an inactive state. In the illustrated embodiment, the oven vent assembly 26 performs this function by positioning the flaps 25 in a substantially open position during any inactive oven condition. For the purposes of this description, an "active" oven condition is defined as an oven condition wherein the oven heater 18 is subject to control for the purpose of establishing or maintaining a selected oven temperature. It is noted that in some embodiments, the heater 18 may be cycled between "on" and "off" states at various times during such an active oven condition. Hence, an "inactive" oven condition is defined as an operating condition other than an active oven condition and as indicated in the state diagram 100 as the inactive oven condition 111. A "transitional" oven condition occurs in the progress from an inactive oven condition to an active oven condition and as indicated in the state diagram 100 as the inactive oven condition 112.

In a particular embodiment, the computer 22 is programmed to operate the oven vent assembly 26 to allow an exchange of cavity air with ambient air during the transitional oven condition 112.

In still another embodiment, it may be appreciated that the oven fan assembly 28 may be activated under control of the computer 22 during any of the above-described oven conditions. In the inactive and transitional oven conditions, activation of the oven fan 31 establishes an elevated pressure proximate to the exhaust port 32 so as to facilitate the exchange of air through the intake and exhaust ports 33, 32 between the oven cavity 17 and the ambient air.

In a particularly preferred embodiment, and during a transitional oven condition, the computer 22 causes the chromatograph 10 to effect a waiting period. In doing so, the computer 22 is programmed to operate the oven vent assembly 26 to allow an exchange of cavity air with ambient air, and preferably activates the oven fan 31 to increase the rate of such exchange, while withholding activation of the oven heater 18, for the duration of the waiting period. Operation of the oven heater 18 is withheld during the waiting period so as to prevent ignition of any combustible gas that may be present in the cavity 17 while the exchange takes place.

Accordingly, for the purposes of the present invention, the waiting period is defined as the time sufficient to cause an exchange of cavity air with ambient air so as to reduce the average concentration of combustible gas present in the oven cavity 17 to a non-hazardous level. The waiting period in the preferred embodiment is calculated at manufacture and stored in the computer 22 as a predetermined value, preferably in the range of 4 to 6 seconds. However, the duration of such a waiting period in other embodiments may be a differing value, or may be calculated by the computer 22 in real time according to the current operating parameter and certain design parameters, such as the particular dimensions of the oven 16. For example, the oven fan 31 may be idle during some portion of such waiting period, which necessitates a longer period for effecting the exchange of cavity air and ambient air.

At the conclusion of the waiting period, the computer 22 then typically proceeds to operate the oven 16 in an active operating condition. For example, in accordance with the setpoints and operating conditions that may be required for a conventional analytical run, the oven heater 18 may again be operated in a continuous or discontinuous fashion to achieve, for example, an elevated column temperature. Similarly, the position of the flaps 25 may varied with respect to the intake and exhaust ports 33, 32 as necessary to control oven temperature.

While the invention has been described and illustrated with reference to specific embodiments, those skilled in the art will recognize that modification and variations may be made without departing from the principles of the invention as described herein above and set forth in the following claims. For example, whereas FIG. 1 illustrates the oven vent assembly 26 in simplified schematic fashion, it is contemplated that a variety of pneumatic or electromechanical devices may be employed to accomplish the described oven venting function. In the illustrated embodiment, the oven vent assembly 26 is constructed to initiate or terminate the rotation of flaps 25 with respect to the intake and exhaust ports 32, 33. Alternatively, the oven vent assembly 25 may comprise sliding or constricting air valve means in lieu of flaps 25; or the control signal may be provided in another form, depending upon the construction of the oven vent assembly 26, such as a variable flow of electrical current, a digital electronic signal, a variable pneumatic flow or pressure level, or a mechanical force applied by a lever, cable, or similar means. Furthermore, the oven vent assembly 26 may include active means, such as one or more additional fans, mounted on the intake port 33 or exhaust port 32 to effect the above-described exchange of cavity air with ambient air. In the embodiment of the invention of FIG. 1, the intake and exhaust ports can be respectively located at low and high pressure points elsewhere on the oven 16. The shape of the oven 16 as shown is rectangular, but the oven could have other shapes, such as a cylinder wherein the circular faces form the front and rear of the oven. The oven heater 18 may be mounted in a number of places, but it is only important that some air flow is provided across it from the oven fan 31.

What is claimed is:

1. A method of operating an oven in a chromatograph, said chromatograph having a computer for operating said chromatograph according to a plurality of operating conditions, said oven having an oven housing having walls defining a cavity and a volume of cavity air therein, an oven heater selectably operable in response to the computer for heating said cavity air, an oven vent located in said oven housing so as to communicate between said cavity and ambient air, and an oven vent assembly for controlling said exchange, comprising the steps of:

determining one of a plurality of operating conditions of the chromatograph; and in response to a determination of an inactive oven condition, operating the oven vent assembly to allow an exchange of cavity air and ambient air through said oven vent.

2. The method of claim 1, wherein said chromatograph further comprises an oven fan selectably operable in response to the computer for effecting said exchange of cavity air and ambient air, and further comprising the step of operating said oven fan assembly during said inactive oven condition.

3. The method of claim 2, wherein the oven vent further comprises an exhaust port and an intake port, said exhaust port and said intake port being located in said oven housing and extending therethrough so as to communicate between said cavity and ambient air, and further comprising the step of operating said oven fan to effect a positive pressure and a negative pressure at the exhaust port and intake port, respectively.

4. The method of claim 1, wherein in response to a determination of a transitional oven operating condition, further comprising the steps of:

withholding the operation of the oven heater for the duration of a waiting period, and operating the oven vent to effect an exchange of cavity air with ambient air during said waiting period.

5. The method of claim 4, wherein the oven vent further comprises an exhaust port and an intake port, said exhaust port and said intake port being located in said oven housing and extending therethrough so as to communicate between said cavity and ambient air, and further comprising the step of operating said oven fan during said waiting period to effect a positive pressure and a negative pressure at the exhaust port and intake port, respectively.

* * * * *